(12) United States Patent
Straub et al.

(10) Patent No.: US 7,034,017 B2
(45) Date of Patent: Apr. 25, 2006

(54) SUBSTITUTED OXAZOLIDINONES AND THEIR USE IN THE FIELD OF BLOOD COAGULATION

(75) Inventors: Alexander Straub, Wuppertal (DE); Thomas Lampe, Düsseldorf (DE); Josef Pernerstorfer, Wuppertal (DE); Elisabeth Perzborn, Wuppertal (DE); Jens Pohlmann, Wuppertal (DE); Susanne Röhrig, Essen (DE); Karl-Heinz Schlemmer, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 7 days.

(21) Appl. No.: 10/470,861

(22) PCT Filed: Jan. 28, 2002

(86) PCT No.: PCT/EP02/00857

§ 371 (c)(1),
(2), (4) Date: Apr. 9, 2004

(87) PCT Pub. No.: WO01/47919

PCT Pub. Date: Jul. 5, 2001

(65) Prior Publication Data

US 2005/0080081 A1    Apr. 14, 2005

(30) Foreign Application Priority Data

Feb. 9, 2001    (DE) ............................ 101 05 989

(51) Int. Cl.
*A61K 31/5377* (2006.01)
*C07D 413/10* (2006.01)

(52) U.S. Cl. .................. 514/230.8; 544/137; 548/229
(58) Field of Classification Search ............ 544/137; 548/229; 514/230.8
See application file for complete search history.

(56) References Cited

FOREIGN PATENT DOCUMENTS

| EP | 0697408 | 2/1996 |
|---|---|---|
| WO | 9931092 | 6/1999 |
| WO | 9937304 | 7/1999 |
| WO | 9906371 | 11/1999 |
| WO | 0147919 | 7/2001 |

OTHER PUBLICATIONS

Brickner,S., et al., "Synthesis and Antibacterial Activity of U-100592 and U-100766, Two Oxazolidinone Antibacterial Agents," J. Med. Chem., vol. 39(3), pp. 673-679 (Feb. 1996), at p. 674, line 8 and p. 678, lines 54-76.*

Hauptmann, et al., "Synthetic Inhibitors of Thrombin and Factor Xa: From Bench to Bedside," Thrombosis Res. 93, 203-241, (1999).

Al-Obeidi, et al., "Factor Xa Inhibitors by Classical and Combinatorial Chemistry", DDT, 3, 223-231, (1998).

Zhu, et al., "Recent Advances in Inhibitors of Factor Xa in the Prothrombinase Complex", Curr. Opin. in Cardiovas. Pul. & Renal Investigational Drugs, 1, 63-88, (1999).

Al-Obeidi, et al., "Factor Xa Inhibitors", Exp. Opin. Ther. Patents 9, 931-953, (1999).

Kaiser, "Thrombin snd Factor Xa Inhibitors," Drugs of the Future, 23, 423-436, (1998).

Uzan, "Antithromobotic Agents," Emerging Drugs, 3, 189-208, (1998).

* cited by examiner

*Primary Examiner*—Kamal A. Saeed
*Assistant Examiner*—Jason M. Nolan

(57) ABSTRACT

This invention relates to compounds of formula (I)

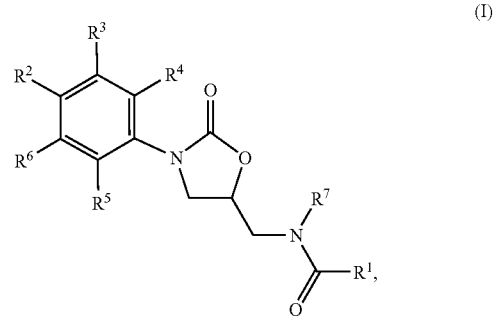

wherein $R^1$ represents optionally substituted phenyl, $R^2$ represents optionally substituted

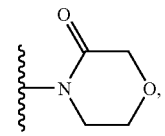

and the remaining "R" groups are as defined in the specification and claims, as well as a method for making such materials, pharmaceutical compositions containing such materials, and methods of using such materials in medical treatment.

10 Claims, No Drawings

SUBSTITUTED OXAZOLIDINONES AND THEIR USE IN THE FIELD OF BLOOD COAGULATION

The present invention relates to the field of blood coagulation. In particular, the present invention relates to novel oxazolidinone derivatives, to processes for their preparation and to their use as active compounds in medicaments.

Blood coagulation is a protective mechanism of the organism which helps to "seal" defects in the wall of the blood vessels quickly and reliably. Thus, loss of blood can be avoided or kept to a minimum. Hemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a joint reaction path, are distinguished. Here factor Xa, which is formed from the proenzyme factor X, plays a key role, since it connects the two coagulation paths. The activated serine protease Xa cleaves prothrombin to thrombin. The resulting thrombin, in turn, cleaves fibrinogen to fibrin, a fibrous/gelatinous coagulant. In addition, thrombin is a potent effector of platelet aggregation which likewise contributes significantly to hemostasis.

Maintenance of normal hemostasis—between bleeding and thrombosis—is subject to a complex regulatory mechanism. Uncontrolled activation of the coagulant system or defective inhibition of the activation processes may cause formation of local thrombi or embolisms in vessels (arteries, veins, lymph vessels) or in heart cavities. This may lead to serious disorders, such as myocardial infarct, angina pectoris (including unstable angina), reocclusions and restenoses after angioplasty or aortocoronary bypass, stroke, transitory ischemic attacks, peripheral arterial occlusive disorders, pulmonary embolisms or deep vein thromboses; hereinbelow, these disorders are collectively also referred to as thromboembolic disorders. In addition, in the case of consumption coagulopathy, hypercoagulability may—systemically—result in disseminated intravascular coagulation.

These thromboembolic disorders are the most frequent cause of morbidity and mortality in most industrialized countries (Pschyrembel, Klinisches Wörterbuch [Clinical Dictionary], 257$^{th}$ edition, 1994, Walter de Gruyter Verlag, page 199 ff., entry "Blutgerinnung" [Blood Coagulation]; Römpp Lexikon Chemie, Version 1.5, 1998, Georg Thieme Verlag Stuttgart, entry "Blutgerinnung"; Lubert Stryer, Biochemie [Biochemistry], Spektrum der Wissenschaft Verlagsgesellschaft mbH Heidelberg, 1990, page 259 ff.).

The anticoagulants, i.e. substances for inhibiting or preventing blood coagulation, which are known from the prior art have various, often grave disadvantages. Accordingly, in practice, an efficient treatment method or prophylaxis of thromboembolic disorders is very difficult and unsatisfactory.

In the therapy and prophylaxis of thromboembolic disorders, use is firstly made of heparin, which is administered parenterally or subcutaneously. Owing to more favorable pharmacokinetic properties, preference is nowadays more and more given to low-molecular-weight heparin; however, even with low-molecular-weight heparin, it is not possible to avoid the known disadvantages described below, which are involved in heparin therapy. Thus, heparin is ineffective when administered orally and has a relatively short half-life. Since heparin inhibits a plurality of factors of the blood coagulation cascade at the same time, the action is nonselective. Moreover, there is a high risk of bleeding; in particular, brain hemorrhages and gastrointestinal bleeding may occur, which may result in thrombopenia, drug-induced alopecia or osteoporosis (Pschyrembel, Klinisches Wörterbuch, 257$^{th}$ edition, 1994, Walter de Gruyter Verlag, page 610, entry "Heparin"; Römpp Lexikon Chemie, Version 1.5, 1998, Georg Thieme Verlag Stuttgart, entry "Heparin").

A second class of anticoagulants are the vitamin K antagonists. These include, for example, 1,3-indanediones, and especially compounds such as warfarin, phenprocoumon, dicumarol and other coumarin derivatives which inhibit the synthesis of various products of certain vitamin K-dependent coagulation factors in the liver in a nonselective manner. Owing to the mechanism of action, however, the onset of the action is very slow (latency to the onset of action 36 to 48 hours). It is possible to administer the compounds orally; however, owing to the high risk of bleeding and the narrow therapeutic index, a time-consuming individual adjustment and monitoring of the patient are required. Moreover, other adverse effects, such as gastrointestinal disturbances, hair loss and skin necroses, have been described (Pschyrembel, Klinisches Wörterbuch, 257$^{th}$ edition, 1994, Walter de Gruyter Verlag, page 292 ff., entry "coumarin derivatives"; Ullmann's Encyclopedia of Industrial Chemistry, 5$^{th}$ edition, VCH Verlagsgesellschaft, Weinheim, 1985–1996, entry "vitamin K").

Recently, a novel therapeutic approach for the treatment and prophylaxis of thromboembolic disorders has been described. This novel therapeutic approach aims to inhibit factor Xa (cf. WO-A-99/37304; WO-A-99/06371; J. Hauptmann, J. Stürzebecher, Thrombosis Research 1999, 93, 203; F. Al-Obeidi, J. A. Ostrem, Factor Xa inhibitors by classical and combinatorial chemistry, DDT 1998, 3, 223; F. Al-Obeidi, J. A. Ostrem, Factor Xa inhibitors, Exp. Opin. Ther. Patents 1999, 9, 931; B. Kaiser, Thrombin and factor Xa inhibitors, Drugs of the Future 1998, 23, 423; A. Uzan, Antithrombotic agents, Emerging Drugs 1998, 3, 189; B.-Y. Zhu, R. M. Scarborough, Curr. Opin. Card. Pulm. Ren. Inv. Drugs 1999, 1 (1), 63). It has been shown that, in animal models, various both peptidic and nonpeptidic compounds are effective as factor Xa inhibitors.

Accordingly, it is an object of the present invention to provide novel substances for controlling disorders, which substances have a wide therapeutic spectrum.

In particular, they should be suitable for a more efficient prophylaxis and/or treatment of thromboembolic disorders, avoiding—at least to some extent—the disadvantages of the prior art described above, where the term "thromboembolic disorders" in the context of the present invention is to be understood as meaning, in particular, serious disorders, such as myocardial infarct, angina pectoris (including unstable angina), reocclusions and restenoses after angioplasty or aortocoronary bypass, stroke, transitory ischemic attacks, peripheral arterial occlusive disorders, pulmonary embolisms or deep venous thromboses.

It is another object of the present invention to provide novel anticoagulants which inhibit the blood coagulation factor Xa with increased selectivity, avoiding—at least to some extent—the problems of the therapeutic methods for thromboembolic disorders known from the prior art.

The present invention provides compounds of the formula (I),

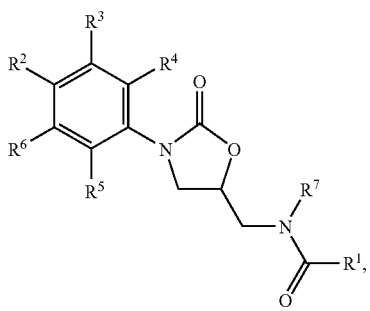

in which

R¹ represents $(C_6–C_{14})$-aryl, 5- to 10-membered heteroaryl having up to three heteroatoms from the group consisting of N, O and S or 5- to 10-membered heterocyclyl having up to three heteroatoms from the group consisting of N, O and S, where the rings may be mono- to trisubstituted, independently of one another, by halogen, $(C_1–C_6)$-alkyl, amino, mono- or di-$(C_1–C_6)$-alkylamino, hydroxyl, $(C_1–C_6)$-alkoxy, $(C_1–C_6)$-alkoxycarbonyl, $(C_1–C_6)$-alkanoyl, trifluoromethyl, trifluoromethoxy, trifluoromethylthio, nitro, oxo, carboxyl or cyano, R² represents a radical —C(O)NR⁸R⁹, —N(R¹⁰)C(O)R¹¹ or

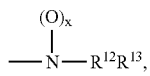

where

R⁸ represents hydrogen, $(C_1–C_6)$-alkyl which for its part may be substituted by halogen, amino, mono- or di-$(C_1–C_6)$-alkylamino, hydroxyl, oxo, $(C_1–C_6)$-alkoxy, trifluoromethyl or cyano, $(C_6–C_{14})$-aryl which for its part may be substituted by halogen, $(C_1–C_6)$-alkyl, amino, mono- or di-$(C_1–C_6)$-alkylamino, hydroxyl, $(C_1–C_6)$-alkoxy, $(C_1–C_6)$-alkoxycarbonyl, $(C_1–C_6)$-alkanoyl, trifluoromethyl, trifluoromethoxy, trifluoromethylthio, nitro, carboxyl or cyano, or $(C_3–C_7)$-cycloalkyl, and R⁹ represents $(C_1–C_6)$-alkyl which for its part may be substituted by halogen, amino, mono- or di-$(C_1–C_6)$-alkylamino, hydroxyl, oxo, $(C_1–C_6)$-alkoxy, trifluoromethyl or cyano, $(C_6–C_{14})$-aryl which for its part may be substituted by halogen, $(C_1–C_6)$-alkyl, amino, mono- or di-$(C_1–C_6)$-alkylamino, hydroxyl, $(C_1–C_6)$-alkoxy, $(C_1–C_6)$-alkoxycarbonyl, $(C_1–C_6)$-alkanoyl, trifluoromethyl, trifluoromethoxy, trifluoromethylthio, nitro, carboxyl or cyano, or $(C_3–C_7)$-cycloalkyl, or R⁸ and R⁹ together with the nitrogen atom to which they are attached form a 4- to 7-membered heterocycle which may contain up to two further heteroatoms from the group consisting of N, O and S and which may furthermore be mono- to trisubstituted, independently of one another, by halogen, $(C_1–C_6)$-alkyl, amino, mono- or di-$(C_1–C_6)$-alkylamino, hydroxyl, oxo, $(C_1–C_6)$-alkoxy, trifluoromethyl or cyano, R¹⁰ and R¹¹, independently of one another, represent $(C_1–C_6)$-alkyl which for its part may be substituted by halogen, amino, mono- or di-$(C_1–C_6)$-alkylamino, hydroxyl, oxo, $(C_1–C_6)$-alkoxy, trifluoromethyl or cyano, $(C_6–C_{14})$-aryl which for its part may be substituted by halogen, $(C_1–C_6)$-alkyl, amino, mono- or di-$(C_1–C_6)$-alkylamino, hydroxyl, $(C_1–C_6)$-alkoxy, $(C_1–C_6)$-alkoxycarbonyl, $(C_1–C_6)$-alkanoyl, trifluoromethyl, trifluoromethoxy, trifluoromethylthio, nitro, carboxyl or cyano, or $(C_3–C_7)$-cycloalkyl, or R¹⁰ and R¹¹ together with the N—C(O) group to which they are attached form a 4- to 7-membered heterocycle which may contain up to two further heteroatoms from the group consisting of N, O and S and which may furthermore be mono- to trisubstituted, independently of one another, by halogen, $(C_1–C_6)$-alkyl, amino, mono- or di-$(C_1–C_6)$-alkylamino, hydroxyl, $(C_1–C_6)$-alkoxy, trifluoromethyl or cyano, x represents 0 or 1, R¹² and R¹³ together with the nitrogen atom to which they are attached form a 4- to 6-membered heterocycle which may contain a further heteroatom from the group consisting of N, O and S and which may be up to disubstituted, independently of one another, by amino, hydroxyl, halogen, trifluoromethyl, cyano, oxo, mono- or di-$(C_1–C_4)$-alkylamino, $(C_1–C_4)$-alkoxy, carboxamido, $(C_1–C_4)$-alkylcarbonyl or $(C_3–C_5)$-cycloalkylcarbonyl, R³, R⁴, R⁵ and R⁶, independently of one another, represent hydrogen, halogen, $(C_1–C_6)$-alkyl, amino, mono- or di-$(C_1–C_6)$-alkylamino, mono- or di-$(C_1–C_6)$-alkylaminocarbonyl, hydroxyl, $(C_1–C_6)$-alkoxy, $(C_1–C_6)$-alkanoyl, $(C_1–C_6)$-alkanoylamino, trifluoromethyl, carbamoyl, nitro or cyano, and R⁷ represents hydrogen or $(C_1–C_6)$-alkyl, and their salts, hydrates, hydrates of the salts and solvates, but excluding compounds of the general formula (I) in which the radical R¹ is an optionally substituted thiophene radical.

To date, oxazolidinones have essentially only been described as antibiotics, and in individual cases also as MAO inhibitors and fibrinogen antagonists (review: Riedl, B., Endermann, R., Exp. Opin. Ther. Patents 1999, 9 (5), 625), where a small 5-[acylaminomethyl] group (preferably 5-[acetylaminomethyl]) appears to be essential for the antibacterial activity.

Substituted aryl- and heteroarylphenyloxazolidinones in which a mono- or polysubstituted phenyl radical may be attached to the N atom of the oxazolidinone ring and which may have an unsubstituted N-methyl-2-thiophenecarboxamide radical in the 5-position of the oxazolidinone ring, and their use as antibacterial substances, are known from U.S. Pat. No. 5,929,248, U.S. Pat. No. 5,801,246, U.S. Pat. No. 5,756,732, U.S. Pat. No. 5,654,435, U.S. Pat. No. 5,654,428 and U.S. Pat. No. 5,565,571.

In addition, benzamidine-containing oxazolidinones are known as synthetic intermediates in the synthesis of factor Xa inhibitors and/or fibrinogen antagonists (WO-A-99/31092, EP-A-623615).

Depending on the substitution pattern, the compounds of the general formula (I) according to the invention may exist in stereoisomeric forms which are either like image and mirror image (enantiomers) or not like image and mirror image (diastereomers). The invention relates both to the enantiomers or diastereomers and to their respective mixtures. The racemic forms, like the diastereomers, can be separated in a known manner into the stereoisomerically uniform components.

Furthermore, certain compounds of the general formula (I) can be present in tautomeric forms. This is known to the person skilled in the art, and such compounds are likewise within the scope of the invention.

Salts of the compounds according to the invention are physiologically acceptable salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, trifluoroacetic acid, propionic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid or naphthalenedisulfonic acid.

Salts may also be physiologically acceptable salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietyl-amine or methylpiperidine.

Moreover, the invention also embraces prodrugs of the compounds according to the invention. According to the invention, prodrugs are those forms of the compounds of the formula (I) which for their part may be biologically active or inactive, but which can be converted into the corresponding biologically active form (for example metabolically or solvolytically) under physiological conditions.

According to the invention, "hydrates" or "solvates" are forms of the compounds of the general formula (I) which form a molecule compound or a complex in the solid or liquid state by hydration with water or coordination with solvent molecules. Examples of hydrates are sesquihydrates, monohydrates, dihydrates or trihydrates. Equally suitable are the hydrates or solvates of salts of the compounds according to the invention.

Halogen represents fluorine, chlorine, bromine and iodine. Preference is given to chlorine, bromine or fluorine.

$(C_1–C_6)$-Alkyl represents a straight-chain or branched alkyl radical having 1 to 6 carbon atoms. Examples which may be mentioned are: methyl, ethyl, n-propyl, isopropyl, n-butyl, isobutyl, tert-butyl, n-pentyl and n-hexyl. The corresponding alkyl groups with fewer carbon atoms, such as, for example, $(C_1–C_4)$-alkyl, are derived analogously from this definition. In general, preference is given to $(C_1–C_4)$-alkyl.

The meaning of the corresponding component of other more complex substituents, such as, for example, in the case of mono- or dialkylamino or mono- or dialkylaminocarbonyl, is likewise derived from this definition.

$(C_3–C_7)$-Cycloalkyl represents a cyclic alkyl radical having 3 to 7 carbon atoms. Examples which may be mentioned are: cyclopropyl, cyclobutyl, cyclopentyl, cyclohexyl or cycloheptyl. Preference is given to cyclopropyl, cyclopentyl and cyclohexyl.

$(C_1–C_6)$-Alkoxy represents a straight-chain or branched alkoxy radical having 1 to 6 carbon atoms. Examples which may be mentioned are: methoxy, ethoxy, n-propoxy, isopropoxy, n-butoxy, isobutoxy, tert-butoxy, n-pentoxy and n-hexoxy. The corresponding alkoxy groups having fewer carbon atoms, such as, for example, $(C_1–C_4)$-alkoxy, are derived analogously from this definition. In general, preference is given to $(C_1–C_4)$-alkoxy.

$(C_1–C_6)$-Alkanoyl represents a straight-chain or branched alkyl radical having 1 to 6 carbon atoms which carries a doubly attached oxygen atom in the 1-position and is attached via the 1-position. Examples which may be mentioned are: formyl, acetyl, propionyl, n-butyryl, i-butyryl, pivaloyl, n-hexanoyl. The corresponding alkanoyl groups with fewer carbon atoms, such as, for example, $(C_1–C_5)$-alkanoyl, $(C_1–C_4)$-alkanoyl and $(C_1–C_3)$-alkanoyl, are derived analogously from this definition. In general, preference is given to $(C_1–C_3)$-alkanoyl.

The meaning of the corresponding component of other more complex substituents, such as, for example, alkanoylamino, is likewise derived from this definition.

$(C_6–C_{14})$-Aryl represents an aromatic radical having 6 to 14 carbon atoms. Examples which may be mentioned are: phenyl, naphthyl, phenanthrenyl and anthracenyl. The corresponding aryl groups with fewer carbon atoms, such as, for example, $(C_6–C_{10})$-aryl are derived analogously from this definition. In general, preference is given to $(C_6–C_{10})$-aryl.

5- to 10-membered heteroaryl having up to 3 heteroatoms from the group consisting of N, O and S represents a mono- or bicyclic, optionally benzofused heteroaromatic which is attached via a carbon ring atom or, via a nitrogen ring atom of the heteroaromatic. Examples which may be mentioned are: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolinyl, indolyl, benzo[b]thienyl, benzo[b]furyl, indazolyl, quinolyl, isoquinolyl, naphthyridinyl, quinazolinyl. The corresponding heteroaromatics having a smaller ring size, such as, for example, 5- to 8-membered heteroaryl, are derived analogously from this definition. In general, preference is given to 5- or 6-membered aromatic heterocycles, such as, for example, pyridyl, pyridyl N-oxide, pyrimidyl, pyridazinyl, furyl and thienyl.

5- to 10-membered heterocyclyl having up to 3 heteroatoms from the group consisting of S, N and O represents a saturated or partially unsaturated mono- or bicyclic, optionally benzofused heterocycle which is attached via a carbon ring atom or a nitrogen ring atom. Examples which may be mentioned are: tetrahydrofuryl, pyrrolidinyl, pyrrolinyl, piperidinyl, 1,2-dihydropyridinyl, 1,4-dihydropyridinyl, piperazinyl, morpholinyl, morpholinyl N-oxide, thiomorpholinyl, azepinyl and 1,4-diazepinyl. Preference is given to piperidinyl, morpholinyl, thiomorpholinyl and pyrrolidinyl.

The corresponding heterocycles having a smaller ring size, such as, for example, 4- to 8-membered heterocycles, are derived analogously from this definition.

Preference is given to compounds of the formula (I), in which $R^1$ represents $(C_6–C_{14})$-aryl, 5- to 10-membered heteroaryl having one nitrogen or oxygen atom as heteroatom and optionally up to two further heteroatoms from the group consisting of N, O and S or 5- to 10-membered heterocyclyl having up to three heteroatoms from the group consisting of N, O and S, where the rings may be mono- to trisubstituted, independently of one another, by halogen, $(C_1–C_6)$-alkyl, amino, mono- or di-$(C_1–C_6)$-alkylamino, hydroxyl, $(C_1–C_6)$-alkoxy, $(C_1–C_6)$-alkoxycarbonyl, $(C_1–C_6)$-alkanoyl, trifluoromethyl, trifluoromethoxy, trifluoromethylthio, nitro, oxo, carboxyl or cyano, $R^2$ represents a radical —C(O)NR$^8$R$^9$, —N(R$^{10}$)C(O)R$^{11}$ or

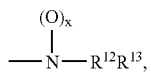

where $R^8$ represents hydrogen,
($C_1$–$C_6$)-alkyl which for its part may be substituted by halogen, amino, mono- or di-($C_1$–$C_6$)-alkylamino, hydroxyl, oxo, ($C_1$–$C_6$)-alkoxy, trifluoromethyl or cyano,
($C_6$–$C_{14}$)-aryl which for its part may be substituted by halogen, ($C_1$–$C_6$)-alkyl, amino, mono- or di-($C_1$–$C_6$)-alkylamino, hydroxyl, ($C_1$–$C_6$)-alkoxy, ($C_1$–$C_6$)-alkoxycarbonyl, ($C_1$–$C_6$)-alkanoyl, trifluoromethyl, trifluoromethoxy, trifluoromethylthio, nitro, carboxyl or cyano, or ($C_3$–$C_7$)-cycloalkyl,
and $R^9$ represents ($C_1$–$C_6$)-alkyl which for its part may be substituted by halogen, amino, mono- or di-($C_1$–$C_6$)-alkylamino, hydroxyl, oxo, ($C_1$–$C_6$)-alkoxy, trifluoromethyl or cyano,
($C_6$–$C_{14}$)-aryl which for its part may be substituted by halogen, ($C_1$–$C_6$)-alkyl, amino, mono- or di-($C_1$–$C_6$)-alkylamino, hydroxyl, ($C_1$–$C_6$)-alkoxy, ($C_1$–$C_6$)-alkoxycarbonyl, ($C_1$–$C_6$)-alkanoyl, trifluoromethyl, trifluoromethoxy, trifluoromethylthio, nitro, carboxyl or cyano, or ($C_3$–$C_7$)-cycloalkyl, or $R^8$ and $R^9$ together with the nitrogen atom to which they are attached form a 4- to 7-membered heterocycle which may contain up to two further heteroatoms from the group consisting of N, O and S and which may furthermore be mono- to trisubstituted, independently of one another, by halogen, ($C_1$–$C_6$)-alkyl, amino, mono- or di-($C_1$–$C_6$)-alkylamino, hydroxyl, oxo, ($C_1$–$C_6$)-alkoxy, trifluoromethyl or cyano, $R^{10}$ and $R^{11}$, independently of one another, represent ($C_1$–$C_6$)-alkyl which for its part may be substituted by halogen, amino, mono- or di-($C_1$–$C_6$)-alkylamino, hydroxyl, oxo, ($C_1$–$C_6$)-alkoxy, trifluoromethyl or cyano, ($C_6$–$C_{14}$)-aryl which for its part may be substituted by halogen, ($C_1$–$C_6$)-alkyl, amino, mono- or di-($C_1$–$C_6$)-alkylamino, hydroxyl, ($C_1$–$C_6$)-alkoxy, ($C_1$–$C_6$)-alkoxycarbonyl, ($C_1$–$C_6$)-alkanoyl, trifluoromethyl, trifluoromethoxy, trifluoromethylthio, nitro, carboxyl or cyano, or ($C_3$–$C_7$)-cycloalkyl, or $R^{10}$ and $R^{11}$ together with the N—C(O) group to which they are attached form a 4- to 7-membered heterocycle which may contain up to two further heteroatoms from the group consisting of N, O and S and which may furthermore be mono- to trisubstituted, independently of one another, by halogen, ($C_1$–$C_6$)-alkyl, amino, mono- or di-($C_1$–$C_6$)-alkylamino, hydroxyl, ($C_1$–$C_6$)-alkoxy, trifluoromethyl or cyano, x represents 0 or 1, $R^{12}$ and $R^{13}$ together with the nitrogen atom to which they are attached form a 4- to 6-membered heterocycle which may contain a further heteroatom from the group consisting of N, O and S and which may be up to disubstituted, independently of one another, by amino, hydroxyl, halogen, trifluoromethyl, cyano, oxo, mono- or di-($C_1$–$C_4$)-alkylamino, ($C_1$–$C_4$)-alkoxy, carboxamido, ($C_1$–$C_4$)-alkylcarbonyl or ($C_3$–$C_5$)-cycloalkylcarbonyl, $R^3$, $R^4$, $R^5$ and $R^6$, independently of one another, represent hydrogen, halogen, ($C_1$–$C_6$)-alkyl, amino, mono- or di-($C_1$–$C_6$)-alkylamino, mono- or di-($C_1$–$C_6$)-alkylaminocarbonyl, hydroxyl, ($C_1$–$C_6$)-alkoxy, ($C_1$–$C_6$)-alkanoyl, ($C_1$–$C_6$)-alkanoylamino, trifluoromethyl, carbamoyl, nitro or cyano, and $R^7$ represents hydrogen or ($C_1$–$C_6$)-alkyl, and their salts, hydrates, hydrates of the salts and solvates.

Particular preference is given to compounds of the formula (I), in which $R^1$ represents phenyl, naphthyl, 5- to 8-membered heteroaryl having one nitrogen or oxygen atom as heteroatom and optionally up to two further heteroatoms from the group consisting of N, O and S or 5- to 8-membered heterocyclyl having up to three heteroatoms from the group consisting of N, O and S, where the rings may be mono- to trisubstituted, independently of one another, by halogen, ($C_1$–$C_6$)-alkyl, ($C_1$–$C_6$)-alkoxy, cyano, trifluoromethyl, trifluoromethoxy or trifluoromethylthio, $R^2$ represents a radical —C(O)NR$^8$R$^9$, —N(R$^{10}$)C(O)R$^{11}$ or

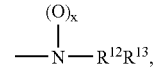

where $R^8$ represents hydrogen, ($C_1$–$C_4$)-alkyl which for its part may be substituted by halogen, amino, mono- or di-($C_1$–$C_4$)-alkylamino, hydroxyl, oxo, ($C_1$–$C_4$)-alkoxy, trifluoromethyl or cyano or ($C_3$–$C_7$)-cycloalkyl, and $R^9$ represents ($C_1$–$C_4$)-alkyl which for its part may be substituted by halogen, amino, mono- or di-($C_1$–$C_4$)-alkylamino, hydroxyl, oxo, ($C_1$–$C_4$)-alkoxy, trifluoromethyl or cyano, or ($C_3$–$C_7$)-cycloalkyl, or $R^8$ and $R^9$ together with the nitrogen atom to which they are attached form a 4- to 7-membered heterocycle which may contain up to two further heteroatoms from the group consisting of N, O and S and which may furthermore be mono- to trisubstituted, independently of one another, by halogen, ($C_1$–$C_6$)-alkyl, amino, mono- or di-($C_1$–$C_6$)-alkylamino, hydroxyl, oxo, ($C_1$–$C_6$)-alkoxy, trifluoromethyl or cyano, $R^{10}$ and $R^{11}$, independently of one another, represent ($C_1$–$C_6$)-alkyl which for its part may be substituted by halogen, amino, mono- or di-($C_1$–$C_6$)-alkylamino, hydroxyl, oxo, ($C_1$–$C_6$)-alkoxy, trifluoromethyl or cyano, or ($C_3$–$C_7$)-cycloalkyl, or $R^{10}$ and $R^{11}$ together with the N—C(O) group to which they are attached form a 4- to 7-membered heterocycle which may contain up to two further heteroatoms from the group consisting of N, O and S and which may furthermore be mono- to trisubstituted, independently of one another, by halogen, ($C_1$–$C_6$)-alkyl, amino, mono- or di-($C_1$–$C_6$)-alkylamino, hydroxyl, ($C_1$–$C_6$)-alkoxy, trifluoromethyl or cyano, x represents 0 or 1, $R^{12}$ and $R^{13}$ together with the nitrogen atom to which they are attached form a 4- to 6-membered heterocycle which may contain a further heteroatom from the group consisting of N, O and S and which may be monosubstituted by amino, hydroxyl, halogen, trifluoromethyl, cyano, oxo, mono- or di-$(C_1–C_4)$-alkylamino, $(C_1–C_4)$-alkoxy, carboxamido, $(C_1–C_4)$-alkylcarbonyl or $(C_3–C_5)$-cycloalkylcarbonyl, $R^3$ and $R^6$, independently of one another, represent hydrogen, halogen, $(C_1–C_6)$-alkyl, amino, mono- or di-$(C_1–C_6)$-alkylamino, hydroxyl, $(C_1–C_6)$-alkoxy, $(C_1–C_6)$-alkanoylamino, cyano, trifluoromethyl or nitro, $R^4$ and $R^5$ represent hydrogen, and $R^7$ represents hydrogen or $(C_1–C_4)$-alkyl, and their salts, hydrates, hydrates of the salts and solvates.

Very particular preference is given to compounds of the formula (I), in which $R^1$ represents phenyl, furyl, dihydrothienyl, thiazolyl, pyrrolyl or pyridyl, where the rings may be mono- to trisubstituted, independently of one another, by fluorine, chlorine, bromine, $(C_1–C_4)$-alkyl, trifluoromethyl, trifluoromethoxy or trifluoromethylthio, $R^2$ represents a radical —C(O)NR$^8$R$^9$, —N(R$^{10}$)C(O)R$^{11}$ or

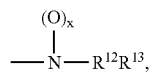

where $R^8$ and $R^9$, independently of one another, represent $(C_1–C_4)$-alkyl which for its part may be substituted by halogen, amino, mono- or di-$(C_1–C_4)$-alkylamino, hydroxyl, oxo, $(C_1–C_4)$-alkoxy, trifluoromethyl or cyano, or $(C_3–C_7)$-cycloalkyl, or $R^8$ and $R^9$ together with the nitrogen atom to which they are attached represent morpholinyl, pyrrolidinyl, thiomorpholinyl or piperidinyl, where the rings may be mono- or disubstituted by $(C_1–C_4)$-alkyl and/or oxo, $R^{10}$ and $R^{11}$, independently of one another, represent $(C_1–C_6)$-alkyl which for its part may be substituted by halogen, amino, mono- or di-$(C_1–C_6)$-alkylamino, hydroxyl, oxo, $(C_1–C_6)$-alkoxy, trifluoromethyl or cyano, or $(C_3–C_7)$-cycloalkyl, or $R^{10}$ and $R^{11}$ together with the N—C(O) group to which they are attached represent morpholinonyl, pyrrolidinonyl, thiomorpholinonyl or piperidinonyl, where the rings may be mono- or disubstituted by $(C_1–C_4)$-alkyl, x represents 0 or 1, $R^{12}$ and $R^{13}$ together with the nitrogen atom to which they are attached form a 5- or 6-membered saturated heterocycle which may contain a further oxygen atom in the ring and which may be monosubstituted by amino or hydroxyl, $R^3$ represents hydrogen, fluorine, chlorine, bromine, $(C_1–C_4)$-alkyl, amino, mono- or di-$(C_1–C_3)$-alkylamino, cyano or nitro, $R^4$, $R^5$ and $R^6$ represent hydrogen, and $R^7$ represents hydrogen, and their salts, hydrates, hydrates of the salts and solvates.

The present invention also provides a process for preparing the compounds of the general formula (I) according to the invention where compounds of the formula (II)

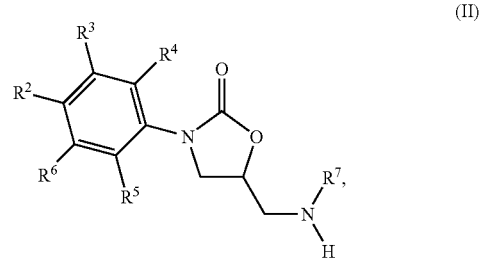

in which $R^2$, $R^3$, $R^4$, $R^5$, $R^6$ and $R^7$ are as defined above are reacted with carboxylic acids of the formula (III)

in which $R^1$ is as defined above, or else with the corresponding carbonyl halides, preferably carbonyl chlorides, or else with the corresponding symmetric or mixed carboxylic anhydrides of the carboxylic acids of the formula (III) defined above in inert solvents, if appropriate in the presence of auxiliaries and/or bases, to give compounds of the formula (I).

Solvents suitable for the process described above are organic solvents which are inert under the reaction conditions. These include halogenated hydrocarbons, such as dichloromethane, trichloromethane, carbon tetrachloride or 1,2-dichloroethane, ethers, such as diethyl ether, dioxane or tetrahydrofuran, or other solvents, such as ethyl acetate, dimethylformamide, acetonitrile, pyridine, N-methylpyrrolidone (NMP) or dimethylacetamide.

It is also possible to use solvent mixtures of the solvents mentioned above.

Suitable for use as auxiliaries for the formation of the amide are customary condensing agents and/or activating agents, such as carbodiimides, for example N'-(3-dimethylaminopropyl)-N-ethylcarbodiimide.HCl (EDC), N,N'-dicyclohexylcarbodiimide (DCC), if appropriate in the presence of 1-hydroxy-1H-benzotriazole.H$_2$O (HOBt), benzotriazol-1-yloxytrispyrrolidinophosphonium hexafluorophosphate (PyBOP®), 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), 2-(2-oxo-1-(2R)-pyridyl-1,1,3,3-tetramethyluronium tetrafluoroborate (TPTU) or O-(7-azabenzotriazol-1-yl)-N,N,N',N'-tetramethyluronium hexafluorophosphate (HATU), or carbonyl compounds, such as carbonyldiimidazole.

Suitable for use as bases are trialkylamines, for example triethylamine, N-methylmorpholine (NMM), N-methylpiperidine, diisopropylethylamine (Hünig base) or 4-N,N-dimethylaminopyridine (DMAP) or pyridine.

The reactions are generally carried out in a temperature range of from 0° C. to the reflux temperature, preferably in the range of from 0° C. to room temperature.

The reactions can be carried out under atmospheric, elevated or reduced pressure (for example in the range of from 0.5 to 5 bar). In general, the reactions are carried out under atmospheric pressure.

The compounds of the general formulae (II) and (III) are known per se to the person skilled in the art or can be prepared by customary methods. For oxazolidinones, in particular the 5-(aminomethyl)-2-oxooxazolidines required, cf. WO-A-98/01446; WO-A-93/23384; WO-A-97/03072; J. A. Tucker et al., J. Med. Chem. 1998, 41, 3727; S. J. Brickner et al., J. Med. Chem. 1996, 39, 673; W. A. Gregory et al., J. Med. Chem. 1989, 32, 1673.

The compounds of the general formula (I) according to the invention have an unforeseeable useful pharmacological activity spectrum and are therefore particularly suitable for the prophylaxis and/or treatment of disorders.

The compounds of the general formula (I) according to the invention act in particular as anticoagulants and can therefore preferably be employed in medicaments for the prophylaxis and/or therapy of thromboembolic disorders. For the purpose of the present invention, "thromboembolic disorders" include, in particular, serious disorders such as myocardial infarct, angina pectoris (including unstable angina), reocclusions and restenoses after angioplasty or aortocoronary bypass, stroke, transitory ischemic attacks, peripheral arterial occlusion disorders, pulmonary embolisms or deep vein thromboses.

Furthermore, the compounds of the general formula (I) according to the invention are also suitable for treating disseminated intravascular coagulation (DIC).

Finally, the compounds of the general formula (I) according to the invention are also suitable for the prophylaxis and/or treatment of atherosclerosis and arthritis, and additionally also for the prophylaxis and/or treatment of Alzheimer's disease and cancer.

Furthermore, the present invention also includes a method for preventing blood coagulation in vitro, in particular in banked blood or biological samples which contain factor Xa, which method is characterized in that compounds of the general formula (I) are added.

The compounds of the general formula (I) according to the invention act in particular as selective inhibitors of the blood coagulation factor Xa and do not inhibit, or only inhibit at considerably higher concentrations, other serine proteases as well, such as thrombin, plasmin or trypsin.

In the context of the present invention, inhibitors of the blood coagulation factor Xa in which the $IC_{50}$ values for the factor Xa inhibition are lower by a factor of 100, preferably by a factor of 500, in particular by a factor of 1000, than the $IC_{50}$ values for the inhibition of other serine proteases, in particular thrombin, plasmin and trypsin, are referred to as being "selective", where with a view to the test methods for selectivity, reference is made to the test methods of Examples A-1) a.1) and a.2) described below.

All customary administration forms are suitable for administration of the compounds according to the invention. Administration is preferably carried out orally, lingually, sublingually, buccally, rectally or parenterally (i.e. bypassing the intestinal tract, that is intravenously, intraarterially, intracardially, intracutaneously, subcutaneously, transdermally, intraperitoneally or intramuscularly). Particularly suitable are oral and intravenous administration. Very particular preference is given to oral administration, this being a further advantage with respect to the prior-art therapy of thromboembolic disorders.

The novel active compounds of the general formula (I) can be converted in a known manner into the customary formulations, such as tablets, sugar-coated tablets, pills, granules, aerosols, syrups, emulsions, suspensions and solutions, using inert non-toxic pharmaceutically suitable excipients or solvents. Here, the therapeutically active compound should in each case be present in a concentration of from about 0.1 to 95% by weight, preferably from 0.5 to 90% by weight, in particular from 1 to 85% by weight, of the total mixture, i.e. in amounts which are sufficient in order to achieve the dosage range indicated.

In spite of this, if appropriate, it may be necessary to depart from the amounts mentioned, namely depending on the body weight or on the type of administration route, on the individual response to the medicament, on the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual administrations over the course of the day.

The formulations are prepared, for example, by extending the active compounds with solvents and/or excipients, if appropriate using emulsifiers and/or dispersants, it being possible, for example if the diluent used is water, optionally to use organic solvents as auxiliary solvents.

In general it has proved advantageous in the case of intravenous administration to administer amounts from approximately 0.001 to 10 mg/kg, preferably approximately 0.01 to 10 mg/kg, in particular approximately 0.1 to 8 mg/kg, of body weight to achieve effective results.

In general, it has proved advantageous in the case of oral administration to administer amounts from approximately 0.01 to 50 mg/kg, preferably approximately 0.1 to 10 mg/kg, in particular approximately 0.5 to 8 mg/kg, of body weight to achieve effective results.

In spite of this, if appropriate, it may be necessary in the case of intravenous or oral administration to depart from the amounts mentioned, namely depending on the body weight or on the type of administration route, on the individual response to the medicament, on the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these over the course of the day, namely into several individual doses or as a continuous infusion.

Compared to the conventional preparations for treating thromboembolic disorders, the compounds of the general formula (I) according to the invention are distinguished in particular by the fact that a greater therapeutic range is achieved by the selective inhibition of factor Xa. For the patient, this means a lower risk of bleeding, and for the treating physician, this means that the patient is easier to adjust. Moreover—owing to the mechanism—the onset of action is more rapid. Above all, however, the compounds according to the invention permit an oral administration form, which is a further advantage of the therapy with the compounds according to the invention.

The present invention is illustrated by the examples below.

A EVALUATION OF THE PHYSIOLOGICAL ACTIVITY

1. General Test Methods

The particularly advantageous biological properties of the compounds according to the invention can be determined by the following methods.

a) Test Description (In Vitro)

a.1) Determination of the Factor Xa Inhibition

The enzymatic activity of human factor Xa (FXa) was measured using the conversion of a chromogenic substrate specific for FXa. Factor Xa cleaves p-nitroaniline from the chromogenic substrate. The determinations were carried out in microtiter plates as follows.

The test substances, in various concentrations, were dissolved in DMSO and incubated at 25° C. with human FXa (0.5 nmol/l dissolved in 50 mmol/l of tris buffer [C,C,C-tris (hydroxymethyl)aminomethane], 150 mmol/l of NaCl, 0.1% BSA (bovine serum albumin), pH=8.3) for 10 minutes. Pure DMSO was used as control. The chromogenic substrate (150 µmol/l of Pefachrome® FXa from Pentapharm) was then added. After an incubation time of 20 minutes at 25° C., the extinction at 405 nm was determined. The extinctions of the test mixtures containing test substance were compared with the control mixtures without test substance, and the $IC_{50}$ values were calculated from these data.

| Example | $IC_{50}$ |
|---|---|
| 1 | 20 nM |
| 6 | 26 nM | a.2) Determination of the Selectivity

To assess selective FXa inhibition, the test substances were examined for their inhibition of other human serine proteases such as thrombin, trypsin and plasmin. To determine the enzymatic activity of thrombin (75 mU/ml), trypsin (500 mU/ml) and plasmin (3.2 nmol/l), these enzymes were dissolved in tris buffer (100 mmol/l, 20 mmol/l $CaCl_2$, pH=8.0) and incubated with test substance or solvent for 10 minutes. The enzymatic reaction was then started by adding the corresponding specific chromogenic substrates (Chromozym Thrombin® from Boehringer Mannheim, Chromozym Trypsin® from Boehringer Mannheim, Chromozym Plasmin® from Boehringer Mannheim) and the extinction at 405 nm was determined after 20 minutes. All determinations were carried out at 37° C. The extinctions of the test mixtures containing test substance were compared with the control samples without test substance, and the $IC_{50}$ values were calculated from these data.

a.3) Determination of the Anticoagulant Action

The anticoagulant action of the test substances was determined in vitro in human plasma. To this end, human blood was drawn off in a mixing ratio of sodium citrate/blood of 1/9 using a 0.11 molar sodium citrate solution as receiver. Immediately after the blood had been drawn off, it was mixed thoroughly and centrifuged at about 2000 g for 10 minutes. The supernatant was pipetted off. The prothrombin time (PT, synonyms: thromboplastin time, quick test) was determined in the presence of varying concentrations of test substance or the corresponding solvent using a commercial test kit (Neoplastin® from Boehringer Mannheim). The test compounds were incubated with the plasma at 37° C. for 10 minutes. Coagulation was then started by addition of thromboplastin, and the time when coagulation occurred was determined. The concentration of test substance which effected a doubling of the prothrombin time was determined.

b) Determination of the Antithrombotic Activity (In Vivo)

b.1) Arteriovenous Shunt Model (Rat)

Fasting male rats (strain: HSD CPB:WU) having a weight of 200–250 g were anesthetized using a Rompun/Ketavet solution (12 mg/kg/50 mg/kg). Thrombus formation was initiated in an arteriovenous shunt in accordance with the method described by Christopher N. Berry et al., Br. J. Pharmacol. (1994), 113, 1209–1214. To this end, the left jugular vein and the right carotid artery were exposed. The two vessels were connected by an extracorporeal shunt using a polyethylene tube (PE 60) of a length of 10 cm. In the middle, this polyethylene tube was attached to a further polyethylene tube (PE 160) of a length of 3 cm which contained a roughened nylon thread which had been arranged to form a loop, to form a thrombogenic surface. The extracorporeal circulation was maintained for 15 minutes. The shunt was then removed and the nylon thread with the thrombus was weighed immediately. The weight of the nylon thread on its own had been determined before the experiment was started. Before the extracorporeal circulation was set up, the test substances were administered to the animals while awake either intravenously via the tail vein or orally using a pharyngeal tube.

b.2) Arterial Thrombosis Model (Rat)

Male fasting rats (strain: HSD CPB: WU) were anesthetized as described above. On average, the rats had a weight of about 200 g. The left carotid artery was exposed (about 2 cm). The formation of an arterial thrombus was induced by mechanical injury to the blood vessel in accordance with the method described by K. Meng et al., Naunyn-Schmiedeberg's Arch. Pharmacol. (1977), 301, 115–119. To this end, the exposed carotid artery was clamped from the blood flow, cooled to −12° C. in a metal trough for 2 minutes and, to standardize the size of the thrombi, simultaneously compressed using a weight of 200 g. The blood flow was then additionally reduced by a clip which was placed around the carotid artery distally from the injured section of the vessel. The proximal clamp was removed, and the wound was closed and re-opened after 4 hours to remove the injured section of the vessel. The section of the vessel was opened longitudinally and the thrombus was removed from the injured section of the vessel. The moist weight of the thrombi was determined immediately. The test substances were administered to the animals while awake at the beginning of the experiment, either intravenously via the tail vein or orally using a pharyngeal tube.

b.3) Venous Thrombosis Model (Rat)

Male fasting rats (strain: HSD CPB: WU) were anesthetized as described above. On average, the rats had a weight of about 200 g. The left jugular vein was exposed (about 2 cm). The formation of a venous thrombus was induced by mechanical injury to the blood vessel in accordance with the method described by K. Meng et al., Naunyn-Schmiedeberg's Arch. Pharmacol. (1977), 301, 115–119. To this end, the jugular vein was clamped from the blood flow, cooled to −12° C. in a metal trough for 2 minutes and, to standardize the size of the thrombi, simultaneously compressed using a weight of 200 g. The blood flow was re-opened and the wound was closed. After 4 hours, the wound was re-opened to remove the thrombi from the injured sections of the vessel. The moist weight of the thrombi was determined immediately. The test substances were administered to the animals while awake at the beginning of the experiment, either intravenously via the tail vein or orally using a pharyngeal tube.

B PREPARATION EXAMPLES

HPLC Parameters:

[1] Column: Kromasil C18 60*2, L-R temperature: 30° C., flow rate=0.75 mlmin$^{-1}$, mobile phase: A=0.01 M $H_3PO_4$, B=$CH_3CN$, gradient: ->0.5 min 90% A->4.5 min 10% A->6.5 min 10% A.

[2] Column: Kromasil C18 60*2, L-R temperature: 30° C., flow rate=0.75 mlmin$^{-1}$, mobile phase: A=0.005 M HClO$_4$, B=CH$_3$CN, gradient: ->0.5 min 98% A->4.5 min 10% A->6.5 min 10% A.

[3] Column: Symmetry C18 2.1×150 mm, column oven: 50° C., flow rate=0.6 mlmin$^{-1}$, mobile phase: A=0.6 g 30% strength HCl/l water, B=CH$_3$CN, gradient: 0.0 min 90% A->4.0 min 10% A->9 min 10% A.

[4] MHZ-2P, Instrument Micromass Platform LCZ Column Symmetry C18, 50 mm×2.1 mm, 3.5 µm, temperature: 40° C., flow rate=0.5 mlmin$^{-1}$, mobile phase A=CH$_3$CN+ 0.1% formic acid, mobile phase B=water+0.1% formic acid, gradient: 0.0 min 10% A->4 min 90% A->6 min 90% A.

Starting Materials

Example I 4-(4-Morpholin-3-onyl)aniline

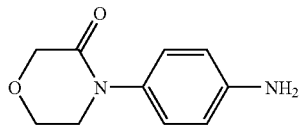

I-a 4-(4-Morpholin-3-onyl)nitrobenzene

The preparation of morpholin-3-one is described in U.S. Pat. No. 5,349,045.

Over a period of 2 hours, sodium hydride (88 g, 2.2 mol, 60% in paraffin) is added a little at a time to a solution of morpholin-3-one (202 g, 2 mol) in N-methylpyrrolidone (2 l). After the evolution of hydrogen has ceased, 4-fluoronitrobenzene (282 g, 2 mol) is added dropwise with cooling over a period of one hour, and the reaction mixture is stirred overnight. At 12 mbar and 76° C., 1.7 l of the volume of the liquid is then distilled off, the residue is poured into water (2 l) and this mixture is extracted twice with ethyl acetate (in each case 1 l). The combined organic phases are washed with water, dried over sodium sulfate, filtered and concentrated under reduced pressure. Purification is carried out by chromatography (on silica gel, hexane/ethyl acetate 1:1) and subsequent crystallization from ethyl acetate. Yield: 78 g (colorless to brownish solid), 17.6% of theory.

$^1$H NMR (300 MHz, CDCl$_3$): 3.86 (m, 2 H, CH$_2$CH$_2$), 4.08 (m, 2 H, CH$_2$CH$_2$), 4.49 (s, 2 H, CH$_2$CO), 7.61 (d, 2 H, $^3$J=8.95 Hz, CHCH), 8.28 (d, 2 H, $^3$J=8.95 Hz, CHCH); MS (r.I. %)=222 (74, M$^+$), 193 (100), 164 (28), 150 (21), 136 (61), 117 (22), 106 (24), 90 (37), 76 (38), 63 (32), 50 (25).

I-b 4-(4-Morpholin-3-onyl)aniline

In an autoclave, 4-(4-morpholin-3-onyl)nitrobenzene (63 g, 0.275 mol) is dissolved in tetrahydrofuran (200 ml), Pd/C (3.1 g, 5%) is added and the mixture is hydrogenated at 70° C. and a hydrogen pressure of 50 bar for 8 hours. The catalyst is filtered off and the solvent is then distilled off under reduced pressure and the product is purified by crystallization from ethyl acetate. Yield: 20 g (colorless to bluish solid), 37.6% of theory. Alternatively, purification can also be carried out by chromatography (on silica gel, hexane/ ethyl acetate mixture).

$^1$H NMR (300 MHz, CDCl$_3$): 3.67 (m, 2H, CH$_2$CH$_2$), 3.99 (m, 2H, CH$_2$CH$_2$), 4.27 (s, 2 H, CH$_2$CO), 6.68 (d, 2 H, $^3$J=8.71 Hz, CHCH), 7.03 (d, 2 H, $^3$J=8.71 Hz, CHCH); MS (r.I. %)=192 (100, M$^+$), 163 (48), 133 (26), 119 (76), 106 (49), 92 (38), 67 (27), 65 (45), 52 (22), 28 (22).

Example II

4-{4-[(5S)-5-(Aminomethyl)-2-oxo-1,3-oxazolidin-3-yl]phenyl}-3-morpholinone

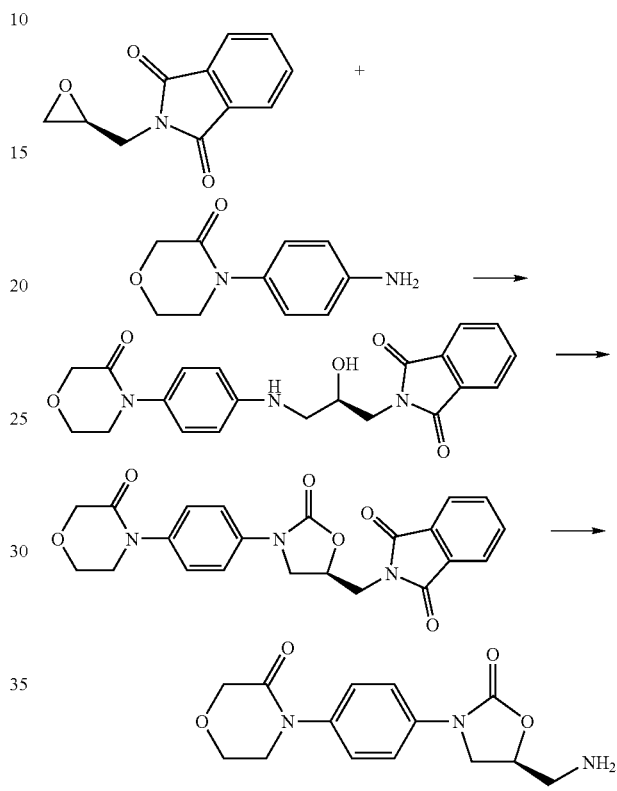

II-a 2-((2R)-2-Hydroxy-3-{[4-(3-oxo-4-morpholinyl)phenyl]amino}propyl)-1H-isoindole-1,3(2H)-dione A suspension of 2-[(2S)-2-oxiranylmethyl]-1H-isoindole-1,3(2H)-dione (A. Gutcait et al. *Tetrahedron Asym.* 1996, 7, 1641) (5.68 g, 27.9 mmol) and 4-(4-aminophenyl)-3-morpholinone (5.37 g, 27.9 mmol) in ethanol/water (9:1, 140 ml) is heated under reflux for 14 hours (the precipitate dissolves; after some time, another precipitate is formed). The precipitate (desired product) is filtered off, washed three times with diethyl ether and dried. The combined mother liquors are concentrated under reduced pressure and, after addition of a second portion of 2-[(2S)-2-oxiranylmethyl]-1H-isoindole-1,3-(2H)-dione (2.84 g, 14.0 mmol), suspended in ethanol/water (9:1, 70 ml) and heated under reflux for 13 hours (the precipitate dissolves; after some time, another precipitate is formed). The precipitate (desired product) is filtered off, washed three times with diethyl ether and dried. Total yield: 10.14 g, 92% of theory.

MS (ESI): m/z (%)=418 ([M+Na]$^+$, 84), 396 ([M+H]$^+$, 93); HPLC (method 2): rt=3.34 min.

II-b 2-({(5S)-2-Oxo-3-[4-(3-oxo-4-morpholinyl)phenyl]-1,3-oxazolidin-5-yl}methyl)-1H-isoindole-1,3(2H)-dione Under argon, N,N'-carbonyldiimidazole (2.94 g, 18.1 mmol) and dimethylaminopyridine (catalytic amount) are added at room temperature to a suspension of the aminoalcohol (3.58 g, 9.05 mmol) in tetrahydrofuran (90 mol). The reaction suspension is stirred at 60° C. for 12 hours (the precipitate dissolves; after some time, another precipitate is formed), a second portion of N,N'-carbonyldiimidazole (2.94 g, 18.1 mmol) is added and the mixture is stirred at 60° C. for another 12 hours. The precipitate (desired product) is filtered off, washed with tetrahydrofuran and dried. The filtrate is concentrated under reduced pressure, and further product is purified by flash chromatography (dichloromethane/methanol mixtures). Total yield: 3.32 g, 87% of theory.

MS (ESI): m/z (%)=422 ([M+H]$^+$, 100); HPLC (method 3): rt=3.37 min.

II-c 4-{4[(5S)-5-Aminomethyl)-2-oxo-1,3-oxazolidine-3-yl]phenyl}-3-morpholinone

At room temperature, methylamine (40% in water, 10.2 ml, 0.142 mol) is added dropwise to a suspension of the oxazolidinone (4.45 g, 10.6 mmol) in ethanol (102 ml). The reaction mixture is heated under reflux for one hour and concentrated under reduced pressure. The crude product is used for the next reaction without further purification.

MS (ESI): m/z (%)=292 ([M+H]$^+$, 100); HPLC (method 2): rt=2.66 min.

Example III (5S)-5-(Aminomethyl)-3-[4-(2-oxo-1-pyrrolidinyl) phenyl]-1,3-oxazolidin-2-one

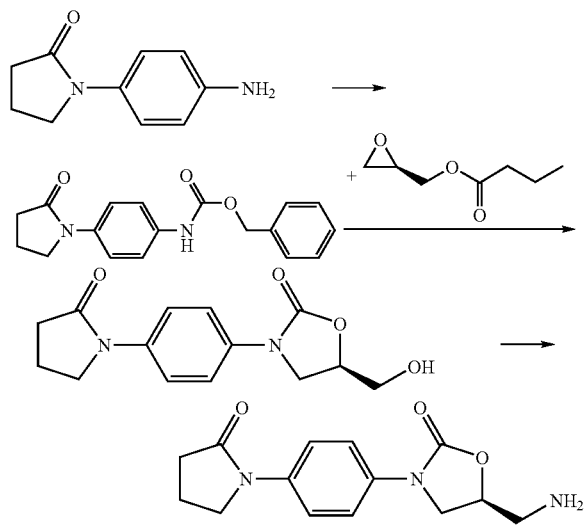

III-a Benzyl 4-(2-oxo-1-pyrrolidinyl)phenylcarbamate

At −20° C., benzyl chloroformate (4.27 g, 25.03 mmol) is slowly added dropwise to 1-(4-aminophenyl)pyrrolidin-2-one (4 g, 22.7 mmol) and N,N-dimethylaniline (3.6 ml, 28.4 mmol) in tetrahydrofuran (107 ml). The reaction mixture is stirred at −20° C. for 30 min and then warmed to room temperature. After addition of ethyl acetate (0.5 l), the organic phase is washed with saturated NaCl solution (0.5 l). The combined organic phase are dried (magnesium sulfate), filtered and concentrated under reduced pressure. The residue is titrated with diethyl ether and filtered off with suction. Yield: 5.2 g, 74% of theory, light-beige crystals, melting point: 174° C.

III-b (5R)-5-(Hydroxymethyl)-3-[4-(2-oxo-1-pyrrolidinyl) phenyl]-1,3-oxazolidin-2-one Under argon, n-butyllithium (7.27 ml, 2.5 M solution in hexane) is, at −10° C., added dropwise to isoamyl alcohol (1.47 g, 16.66 mmol) in tetrahydrofuran (200 ml) and further n-butyllithium is added until the added indicator N-benzylidenebenzylamine changes its color. The reaction mixture is stirred at −10° C. for 10 minutes and cooled to −78° C., and a solution of benzyl 4-(2-oxo-1-pyrrolidinyl)phenylcarbamate (4.7 g, 15.14 mmol) is added slowly, n-Butyllithium (2.5 M solution in hexane) is then added again, until the color of the indicator changes to pink. The reaction mixture is stirred at −78° C. for 10 minutes, R-glycidyl butyrate (2.62 g, 18.17 g) is added and the mixture is stirred at −78° C. for 30 minutes. The reaction mixture is warmed to room temperature overnight, and water (200 ml) is added. The tetrahydrofuran fraction is removed under reduced pressure. The aqueous residue is extracted with ethyl acetate and the combined organic phases are dried with (magnesium sulfate), filtered and concentrated under reduced pressure. The residue is titrated with diethyl ether (500 ml) and the precipitated crystals are filtered off with suction. Yield: 3.76 g, 90% of theory.

Melting point: 148° C., $R_f$ (SiO$_2$, toluene/ethyl acetate 1:1)=0.04, (starting material=0.3).

III-c (5S)-5-(Aminomethyl)-3-[4-(2-oxo-1-pyrrolidinyl) phenyl]-1,3-oxazolidin-2-one At 0° C., methanesulfonyl chloride (1.79 g, 15.64 mmol) is added to a solution of (5R)-5-(hydroxymethyl)-3-[4-(2-oxo-1-pyrrolidinyl)phenyl]-1,3-oxazolidin-2-one (3.6 g, 13.0 mmol) and triethylamine (2.9 g, 28.7 mmol) in dichloromethane (160 ml). The reaction mixture is stirred at 0° C. for 1.5 hours and at room temperature for 3 hours and then washed with water, and the aqueous phase is reextracted with dichloromethane. The combined organic phases are dried (magnesium sulfate), filtered and concentrated under reduced pressure. The residue (1.67 g) is then dissolved in acetonitrile (70 ml), phthalimide potassium (2.62 g, 14.16 mmol) is added and the mixture is stirred in a closed vessel in a microwave oven at 180° C. for 45 min. Insoluble material is removed from the mixture by filtration, the filtrate is evaporated under reduced pressure, the residue (1.9 g) is dissolved in methanol and hydrazine hydrate (0.47 g, 9.37 mmol) is added. The reaction mixture is heated under reflux for 2 hours and cooled, saturated sodium bicarbonate solution is added and the mixture is extracted six times with methylene chloride (2 l in total). The combined organic phases are dried (magnesium sulfate), filtered and concentrated under reduced pressure.

The resulting product is used without further purification.

SYNTHESIS EXAMPLES

Example 1

4-Chloro-N-({(5S)-2-oxo-4-[4-(3-oxo-4-morpholinyl)phenyl]-1,3-oxazolidin-5-yl}methyl)benzamide

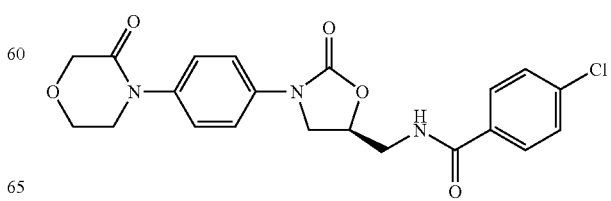

Under argon, 4-chlorobenzoyl chloride (72.1 mg, 0.41 mmol) is added dropwise at room temperature to a solution of the amine II (80.0 mg, 0.27 mmol) in pyridine (2 ml). The reaction mixture is stirred at room temperature for 2 hours and then diluted with pyridine (4 ml), aminomethylpolystyrene resin (2.5 eq.) is added and the mixture is shaken at room temperature for 1.5 hours. The resin is filtered and washed repeatedly with dichloromethane/methanol (5:1). The combined filtrates are concentrated under reduced pressure. The desired product is purified by flash chromatography (dichloromethane/methanol mixtures). Yield: 105.1 mg, 89% of theory.

$^1$H NMR (DMSO-d$^6$, 200 MHz): 8.90 (t, 1H), 7.86 (d, 2H), 7.60–7.50 (m, 4H), 7.40 (d, 2H), 4.92–4.82 (m, 1H), 4.24–4.15 (m, 1H), 4.19 (s, 2H), 4.00–3.93 (m, 2H), 3.93–3.85 (dd, 1H), 3.75–3.68 (m, 2H), 3.68–3.60 (m, 2H); MS (DCI, NH$_3$): m/z (%)=447 ([M+NH$_4$]$^+$, 100); HPLC (method 2): rt=3.76 min.

The following compounds were prepared analogously:

Example 6

5-Bromo-N-({(5S)-2-oxo-3-[4-(3-oxo-4-morpholinyl)phenyl]-1,3-oxazolidin-5-yl}methyl)-2-furamide

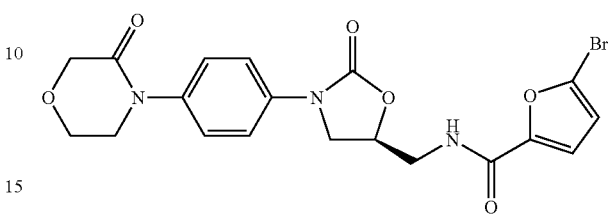

Under argon, N-(3-dimethylaminopropyl)ethylcarbodiimide hydrochloride (79.0 mg, 0.41 mmol) and dropwise, N,N-diisopropylethylamine (120 μl, 0.69 mmol) are added

| Example number | Structure | Mass | HPLC method: retention time |
|---|---|---|---|
| 2 | 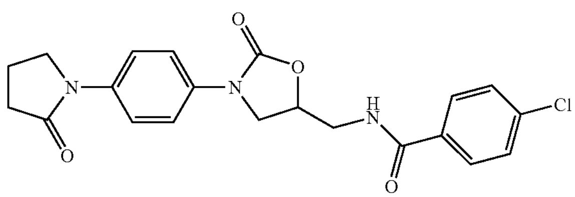 | MS (ESI): m/z. (%) = 414 ([M + H]$^+$, 100) | Method 4: 3.44 min |
| 3 | 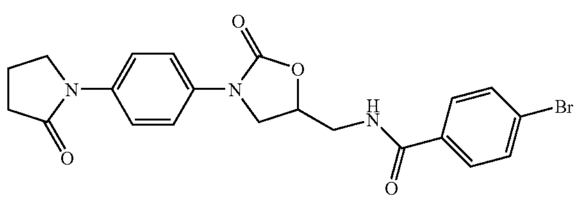 | MS (ESI): m/z (%) = 458/460 ([M + H]$^+$, 100) | Method 4: 3.53 min |
| 4 | 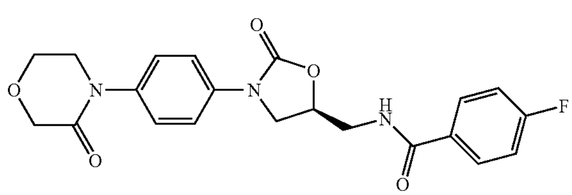 | MS (ESI): m/z (%) = 414 ([M + H]$^+$, 100 | Method 2: 3.57 min |
| 5 | | MS (ESI): m/z (%) = 386 ([M + H]$^+$, 100) | Method 2: 3.24 min | at room temperature to a solution of the amine II (100.0 mg, 0.34 mmol), 5-bromo-2-furancarboxylic acid (78.7 mg, 0.41 mmol) and 1-hydroxy-1H-benzotriazole (55.7 mg, 0.41 mmol) in dimethylformamide (3.4 ml). The reaction mixture was stirred at room temperature for 16 hours and concentrated under reduced pressure. The desired product is purified by flash chromatography (dichloromethane/methanol mixtures).

Yield: 79.6 mg, 50% of theory.

$^1$H NMR (DMSO-d$^6$, 200 MHz): 8.79 (t, 1H), 7.56 (d, 2H), 7.41 (m, 4H), 7.19 (d, 1H), 6.77 (d, 1H) 4.88–4.77 (m, 1H), 4.19 (s, 2H), 4.18 (dd, 1H), 4.00–3.9 (m, 2H), 3.90–3.82 (dd, 1H), 3.75–3.67 (m, 2H), 3.62–3.53 (m, 2H); MS (ESI): m/z (%)=464 ([M+H]$^+$, 100); HPLC (method 1): rt=3.31 min.

The following compounds were prepared analogously:

| Example number | Structure | Mass | HPLC method: retention time |
|---|---|---|---|
| 7 | 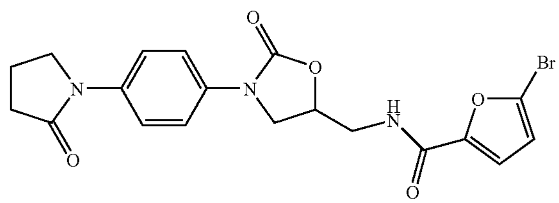 | MS (ESI): m/z (%) = 448 ([M + H]$^+$, 100) | Method 4: 3.18 min |
| 8 | 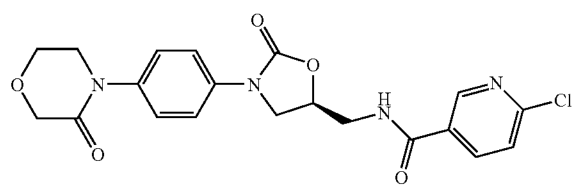 | MS (ESI): m/z (%) = 431 ([M + H]$^+$, 100) | Method 2: 3.46 min |
| 9 | 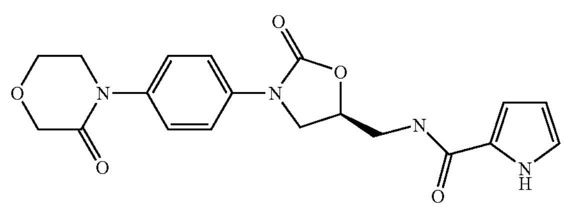 | MS (ESI): m/z (%) = 385 ([M + H]$^+$, 100) | Method 2: 2.57 min |
| 10 | 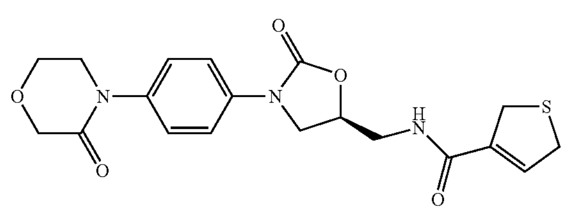 | MS (ESI): m/z (%) = 404 ([M + H]$^+$, 100) | Method 2: 3.40 min |
| 11 | 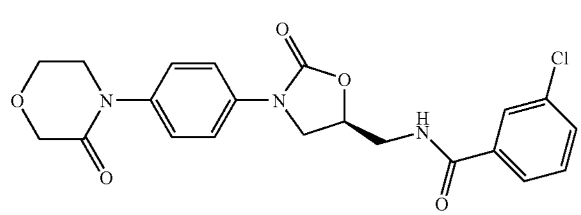 | MS (DCI, NH$_3$): m/z (%) = 447 ([M + NH$_4$]$^+$, 100) | Method 2: 3.76 min |

The invention claimed is:

1. A compound of the formula (I)

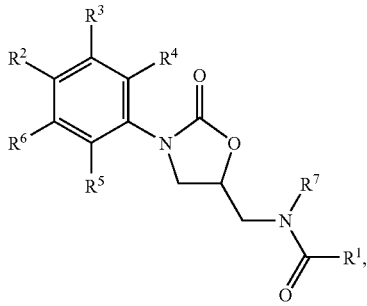

in which
R$^1$ represents phenyl, where the ring may be mono- to trisubstituted, independently of one another, by halogen, (C$_1$–C$_6$)-alkyl, amino, mono- or di-(C$_1$–C$_6$)-alkylamino, hydroxyl, (C$_1$–C$_6$)-alkoxy, (C$_1$–C$_6$)-alkoxycarbonyl, (C$_1$–C$_6$)-alkanoyl, trifluoromethyl, trifluoromethoxy, trifluoromethylthio, nitro, oxo, carboxyl or cyano, R$^2$ represents a radical —N(R$^{10}$)C(O)R$^{11}$, where R$^{10}$ and R$^{11}$ together with the N—C(O) group to which they are attached form a

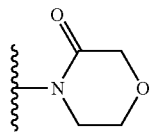

which may furthermore be mono- to trisubstituted, independently of one another, by halogen, (C$_1$–C$_6$)-alkyl, amino, mono- or di-(C$_1$–C$_6$)-alkylamino, hydroxyl, (C$_1$–C$_6$)-alkoxy, trifluoromethyl or cyano, R$^3$, R$^4$, R$^5$ and R$^6$, independently of one another, represent hydrogen, halogen, (C$_1$–C$_6$)-alkyl, amino, mono- or di-(C$_1$–C$_6$)-alkylamino, mono- or di-(C$_1$–C$_6$)-alkylaminocarbonyl, hydroxyl, C$_1$–C$_6$)-alkoxy, C$_1$–C$_6$)-alkanoyl, C$_1$–C$_6$)-alkanoylamino, trifluoromethyl, carbamoyl, nitro or cyano, and R$^7$ represents hydrogen or (C$_1$–C$_6$)-alkyl, or a pharmaceutically acceptable salt, hydrate, hydrate of a salt, or solvate thereof.

2. The compound of the formula (I) as claimed in claim 1, in which
R$^1$ represents phenyl, where the ring may be mono- to trisubstituted, independently of one another, by halogen, (C$_1$–C$_6$)-alkyl, amino, mono- or di-(C$_1$–C$_6$)-alkylamino, hydroxyl, (C$_1$–C$_6$)-alkoxy, (C$_1$–C$_6$)-alkoxycarbonyl, (C$_1$–C$_6$)-alkanoyl, trifluoromethyl, trifluoromethoxy, trifluoromethylthio, nitro, oxo, carboxyl or cyano, R$^2$ represents a radical —N(R$^{10}$)C(O)R$^{11}$
where
R$^{10}$ and R$^{11}$ together with the N—C(O) group to which they are attached form a

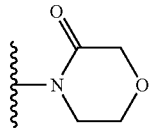

which may furthermore be mono- to trisubstituted, independently of one another, by halogen, (C$_1$–C$_6$)-alkyl, amino, mono- or di-(C$_1$–C$_6$)-alkylamino, hydroxyl, (C$_1$–C$_6$)-alkoxy, trifluoromethyl or cyano, R$^3$, R$^4$, R$^5$ and R$^6$, independently of one another, represent hydrogen, halogen, (C$_1$–C$_6$)-alkyl, amino, mono- or di-(C$_1$–C$_6$)-alkylamino, mono- or di-(C$_1$–C$_6$)-alkylaminocarbonyl, hydroxyl, C$_1$–C$_6$)-alkoxy, (C$_1$–C$_6$)-alkanoyl, (C$_1$–C$_6$)-alkanoylamino, trifluoromethyl, carbamoyl, nitro or cyano, and R$^7$ represents hydrogen or (C$_1$–C$_6$)-alkyl, or a pharmaceutically acceptable salt, hydrate, hydrate of a salt, or solvate thereof.

3. The compound of the formula (I) as claimed in claim 1, in which
R$^1$ represents phenyl, where the ring may be mono- to trisubstituted, independently of one another, by halogen, (C$_1$–C$_6$)-alkyl, (C$_1$–C$_6$)-alkoxy, cyano, trifluoromethyl, trifluoromethoxy or trifluoromethylthio, R$^2$ represents a radical —N(R$^{10}$)C(O)R$^{11}$
where
R$^{10}$ and R$^{11}$ together with the N—C(O) group to which they are attached form a

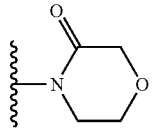

which may furthermore be mono- to trisubstituted, independently of one another, by halogen, (C$_1$–C$_6$)-alkyl, amino, mono- or di-C$_1$–C$_6$)-alkylamino, hydroxyl, (C$_1$–C$_6$)-alkoxy, trifluoromethyl or cyano, R$^3$ and R$^6$, independently of one another, represent hydrogen, halogen, (C$_1$–C$_6$)-alkyl, amino, mono- or di-(C$_1$–C$_6$)-alkylamino, hydroxyl, (C$_1$–C$_6$)-alkoxy, (C$_1$–C$_6$)-alkanoylamino, cyano, trifluoromethyl or nitro, R$^4$ R$^5$ represent hydrogen, and R$^7$ represents hydrogen or (C$_1$–C$_4$)-alkyl, or a pharmaceutically acceptable salt, hydrate, hydrate of a salt, or solvate thereof.

4. The compound of the formula (I) as claimed in claim 1, in which
R$^1$ represents phenyl, where the ring may be mono- to trisubstituted, independently of one another, by fluorine, chlorine, bromine, (C$_1$–C$_4$)-alkyl, trifluoromethyl, trifluoromethoxy or trifluoromethylthio, R$^2$ represents a radical —N(R$^{10}$)C(O)R$^{11}$
where
R$^{10}$ and R$^{11}$ together with the N—C(O) group to which they are attached represent

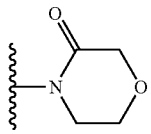

where the ring may be mono- or disubstituted by (C$_1$–C$_4$)-alkyl,

R$^3$ represents hydrogen, fluorine, chlorine, bromine, (C$_1$–C$_4$)-alkyl, amino, mono- or di-(C$_1$–C$_3$)-alkylamino, cyano or nitro, R$^4$, R$^5$ and R$^6$ represent hydrogen, and R$^7$ represents hydrogen, or a pharmaceutically acceptable salt, hydrate, hydrate of a salt, or solvate thereof.

5. A process for preparing compounds of the formula (I) as claimed in claim 1, characterized in that a compound of the formula (II)

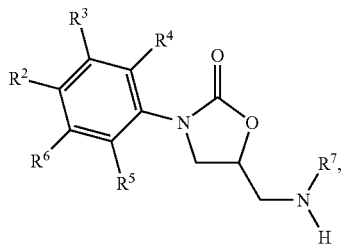

in which R$^2$, R$^3$, R$^4$, R$^5$, R$^6$ and R$^7$ are as defined above in claim 1 is reacted with a carboxylic acid of the formula (III)

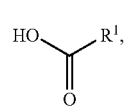

in which R$^1$ is as defined above, or else with the corresponding carbonyl halide or else with the corresponding symmetric or mixed carboxylic anhydride of the carboxylic acid of the formula (III) defined above.

6. A pharmaceutical composition comprising at least one compound of the formula (I) as claimed in claim 1 and at least one further auxiliary.

7. A method for the prevention and/or treatment of a thromboembolic disorder selected from the group consisting of myocardial infarction, angina pectoris (including unstable angina), reocclusions and restenoses after angioplasty or aortocoronay bypass, cerebro vascular accident, transitory ischemic attacks, peripheral occlusive diseases, pulmonary embolisms and deep vein thromboses, comprising administering to a subject an effective amount of a compound of claim 1.

8. A method for the prevention and/or treatment of disseminated intravasal coagulation (DIC) comprising administering to a subject an effective amount of a compound of claim 1.

9. A process for preventing the coagulation of blood in vitro, characterized in that compounds of the general formula (I) as claimed in claim 1 are added to said blood.

10. The process of claim 9 wherein said blood is banked blood or a biological sample containing factor Xa.

* * * * *